(12) United States Patent
Cao et al.

(10) Patent No.: US 11,389,189 B2
(45) Date of Patent: Jul. 19, 2022

(54) ULTRASONIC OSTEOTOME BIT

(71) Applicant: BEIJING SMTP TECHNOLOGY CO., LTD., Beijing (CN)

(72) Inventors: Qun Cao, Beijing (CN); Songtao Zhan, Beijing (CN)

(73) Assignee: Beijing SMTP Technology Co., Ltd., Beijing (CN)

(*) Notice: Subject to any disclaimer, the term of this patent is extended or adjusted under 35 U.S.C. 154(b) by 366 days.

(21) Appl. No.: 16/643,815

(22) PCT Filed: Aug. 12, 2018

(86) PCT No.: PCT/CN2018/100141
§ 371 (c)(1),
(2) Date: Mar. 2, 2020

(87) PCT Pub. No.: WO2019/052295
PCT Pub. Date: Mar. 21, 2019

(65) Prior Publication Data
US 2020/0205850 A1    Jul. 2, 2020

(30) Foreign Application Priority Data
Sep. 14, 2017 (CN) .......................... 201710828655.1

(51) Int. Cl.
*A61B 17/32* (2006.01)
(52) U.S. Cl.
CPC ............ *A61B 17/320068* (2013.01); *A61B 2017/32007* (2017.08); *A61B 2017/320074* (2017.08);
(Continued)
(58) Field of Classification Search
CPC ........... A61B 17/320068; A61B 2017/320077; A61B 17/1644; A61B 2017/1651;
(Continued)

(56) References Cited

U.S. PATENT DOCUMENTS

2016/0374706 A1    12/2016    Cotter et al.

FOREIGN PATENT DOCUMENTS

| CN | 101141923 | 3/2008 |
| CN | 205234577 | 5/2016 |

(Continued)

OTHER PUBLICATIONS

PCT/CN2018/100141, "International Preliminary Report on Patentability", dated Mar. 26, 2020, 11 pages.
(Continued)

*Primary Examiner* — Katherine M Shi
(74) *Attorney, Agent, or Firm* — Kilpatrick Townsend & Stockton LLP

(57) ABSTRACT

Disclosed is an ultrasonic osteotome bit, which comprises a bit bar (1), a bit tip (2), and a liquid injection portion (3), one end of the liquid injection portion (3) being connected to the bit bar (1) and the other end of the liquid injection portion (3) being connected to the bit tip (2), wherein the ultrasonic osteotome bit further comprises a hollow liquid injection channel (10), the hollow liquid injection channel (10) penetrates from a tail end of the bit bar (1) to the liquid injection portion (3) along an axial direction of the bit bar (1), the liquid injection portion (3) is provided with a transverse liquid guide channel (20) penetrating transversely, i.e. substantially perpendicular to an axis of the bit bar (1), the transverse liquid guide channel (20) is in communication with the hollow liquid injection channel (10), and the transverse liquid guide channel (20) forms openings in lateral faces of the liquid injection portion (3). The ultrasonic osteotome bit allows a cooling liquid to sufficiently flow to the bit without being excited or scattered by ultrasonic vibration, thereby ensuring that the bit tip (2) is sufficiently cooled during use.

17 Claims, 7 Drawing Sheets

(52) U.S. Cl.
CPC ............. *A61B 2017/320078* (2017.08); *A61B 2217/005* (2013.01)

(58) Field of Classification Search
CPC .. A61B 2017/320072; A61B 2217/007; A61B 17/144; A61B 2017/32007; A61B 2017/320084; A61B 17/16; A61B 17/1604; A61B 17/1615; A61B 17/1659; A61B 2017/320074; A61B 2017/320075; A61B 2017/1602; A61B 17/32
See application file for complete search history.

(56) References Cited

FOREIGN PATENT DOCUMENTS

| | | |
|---|---|---|
| CN | 106175877 | 12/2016 |
| CN | 106890020 | 6/2017 |
| CN | 107518929 | 12/2017 |
| EP | 2745797 | 6/2014 |
| KR | 100884211 B1 | 2/2009 |
| KR | 20090042837 A | 4/2009 |

OTHER PUBLICATIONS

PCT/CN2018/100141 , "International Search Report and Written Opinion", dated Oct. 16, 2018, 11 pages.

ULTRASONIC OSTEOTOME BIT

CROSS-REFERENCE TO RELATED APPLICATIONS

This application is a U.S. National Stage of International Application No. PCT/CN2018/100141, filed Aug. 12, 2018, which claims the benefit of Chinese Patent Application No. 201710828655.1, filed Sep. 14, 2017. The contents of these applications are hereby incorporated by reference in their entireties for all purposes.

TECHNICAL FIELD

The present invention relates to the technical field of medical appliances, and in particular to an ultrasonic osteotome bit.

BACKGROUND ART

In orthopedic surgery, ultrasonic osteotomes are often used to cut, grind, plane, scrape, or arbitrarily shape bones. Sheet-shaped bits of existing ultrasonic osteotomes are bits which mainly have a cutting function. Such bits conform to the usage habits of surgeons, provide a good hand feel, and have a very suitable cutting speed. However, the cooling of the sheet-shaped bits has always been a major problem. The conventional cooling methods include direct cooling and hollow cooling. FIGS. 16 and 17 show ultrasonic osteotome bits in the prior art. As shown in FIG. 16, an ultrasonic osteotome bit cooled by the conventional direct cooling method comprises a bit bar 1' and a bit tip 2'. Although the direct cooling method is simple and easy, a cooling liquid flow is easily excited and scattered by the bit when dropping, thereby reducing the cooling effect. FIG. 17 shows an ultrasonic osteotome bit cooled by the conventional hollow cooling method, in which a hollow liquid injection groove 10' is formed. Although the cooling liquid can directly reach the bit tip 2' by using the hollow cooling method, the presence of the hollow groove 10' destroys the complete connection structure of the bit, so that the service life of the bit is shortened, and the bit is easily broken into fragments which invade body tissues to cause medical accidents.

SUMMARY OF THE INVENTION

An object of the present invention is to provide an ultrasonic osteotome bit, which comprises a bit bar, a bit tip, and a liquid injection portion, one end of the liquid injection portion being connected to the bit bar and the other end of the liquid injection portion being connected to the bit tip, wherein the ultrasonic osteotome bit further comprises a hollow liquid injection channel, the hollow liquid injection channel penetrates from a tail end of the bit bar to the liquid injection portion along an axis direction of the bit bar, the liquid injection portion is provided with a transverse liquid guide channel penetrating transversely, i.e. substantially perpendicular to an axis of the bit bar, the transverse liquid guide channel is in communication with the hollow liquid injection channel, and the transverse liquid guide channel forms openings in lateral faces of the liquid injection portion.

In the ultrasonic osteotome bit of the present invention, preferably, the liquid injection portion and the bit tip have different thicknesses, and the liquid injection portion is connected to the bit tip via a wedge-shaped transition portion.

In the ultrasonic osteotome bit of the present invention, preferably, the angle between an inclined plane of the wedge-shaped transition portion and an axis direction of the bit tip is less than 10 degrees.

In the ultrasonic osteotome bit of the present invention, preferably, the bit tip is in the shape of a planar sheet with two wide planes being substantially parallel to each other, or a planar wedge with two wide planes forming an angle.

In the ultrasonic osteotome bit of the present invention, preferably, a cutting portion is formed at a front end of the bit tip, and the cutting portion is in the shape of a semicircle, a quarter circle, or a hook.

In the ultrasonic osteotome bit of the present invention, preferably, the bit tip is bent toward one side in a direction perpendicular to the wide planes of the bit tip.

In the ultrasonic osteotome bit of the present invention, preferably, the angle between the bit tip and a central axis of the bit bar is 0 to 30°.

In the ultrasonic osteotome bit of the present invention, preferably, the bit tip is bent toward one side in a direction parallel to the wide planes of the bit tip.

In the ultrasonic osteotome bit of the present invention, preferably, the angle between the bit tip and a central axis of the bit bar is 0 to 45°.

In the ultrasonic osteotome bit of the present invention, preferably, cutting teeth are formed on one side or two sides of a blade of the bit tip.

In the ultrasonic osteotome bit of the present invention, preferably, the cutting teeth are sharp teeth or square teeth, and tooth tips of the cutting teeth all protrude forward in an axial direction of the bit bar.

In the ultrasonic osteotome bit of the present invention, preferably, the liquid injection portion is cylindrical in shape, and is provided with a large part and a small part sequentially formed from the bit bar to the bit tip, two liquid discharge faces substantially parallel to the wide planes of the bit tip are formed on the small part, the two liquid discharge faces are substantially parallel to each other, and the transverse liquid guide channel forms openings in the two liquid discharge faces respectively.

With the above technical solutions, the ultrasonic osteotome bit of the present invention makes the full use of the structural characteristics of the bit, the bit bar is provided with an axial hollow liquid injection channel, and the liquid injection portion is provided with a transverse liquid guide channel, such that an ultrasonic cooling liquid passes through the hollow liquid injection channel and flows out of the openings in the lateral faces of the transverse liquid guide channel. Accordingly, the ultrasonic osteotome bit of the present invention enables the cooling liquid to sufficiently flow to the bit without being excited or scattered by ultrasonic vibration, thereby ensuring that the bit tip is sufficiently cooled during use, and also ensuring the integrity of the bit structure, thereby ensuring the service life of the bit, avoiding the risk of fragmentation of the bit when being broken which may invade body tissues, and improving the surgical safety.

REFERENCE NUMBERS

1', 1—Bit bar, 2', 2—Bit tip, 10'—Hollow groove, 3—Liquid injection portion, 4—Wedge-shaped transition portion, 5—Liquid discharge face, 10—Hollow liquid injection channel, 20—Transverse liquid guide channel, 21—Cutting tooth, 22—Cutting portion, 23—Wide plane, 31—Large part, 32—Small part.

DETAILED DESCRIPTION OF EMBODIMENTS

In order to make the objectives, technical solutions and advantages of the present invention clearer, the technical solutions in the embodiments of the present will be described clearly and completely. It should be understood that the specific embodiments described herein are merely used to explain the present invention, but not to limit the present invention. The embodiments described are merely some of rather than all the embodiments of the present invention. Any other embodiments obtained by those of ordinary skill in the art based on the embodiments of the present invention without any creative effort shall fall within the scope of protection of the present invention.

In the description of the present invention, it should be noted that the orientation or position relationships indicated by the terms "upper", "lower", "transverse", "perpendicular", etc. are based on the orientation or position relationships shown in the accompanying drawings, are intended to facilitate the description of the present invention and simplify the description only, rather than indicating or implying that the devices or elements referred to must have particular orientations or be constructed and operated in particular orientations, and will not to be interpreted as limiting the present invention. The term "wide plane" is relative to a planar wedge, and the terms "large part" and "small part" are also relative to each other.

Moreover, in the description of the present invention, it should be noted that the terms "connecting" and "connection" should be understood in a broad sense, unless otherwise explicitly specified or defined, for example, it may be a fixed connection, a detachable connection or an integrated connection; may be a mechanical connection or an electrical connection; and may be a direct connection or an indirect connection through an intermediate medium, or may be a communication between the interior of two elements. For those of ordinary skill in the art, the specific meanings of the terms mentioned above in the present invention should be construed according to specific circumstances.

The present invention will be further described in detail below by specific embodiments with reference to the accompanying drawings.

Figure 1:
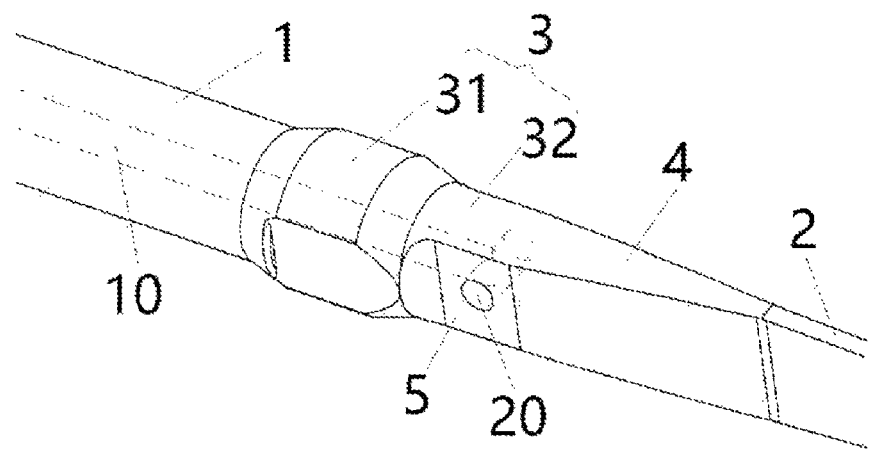
FIG. 1 is a perspective view showing an ultrasonic osteotome bit with a liquid injection portion according to the present invention.
Figure 2:
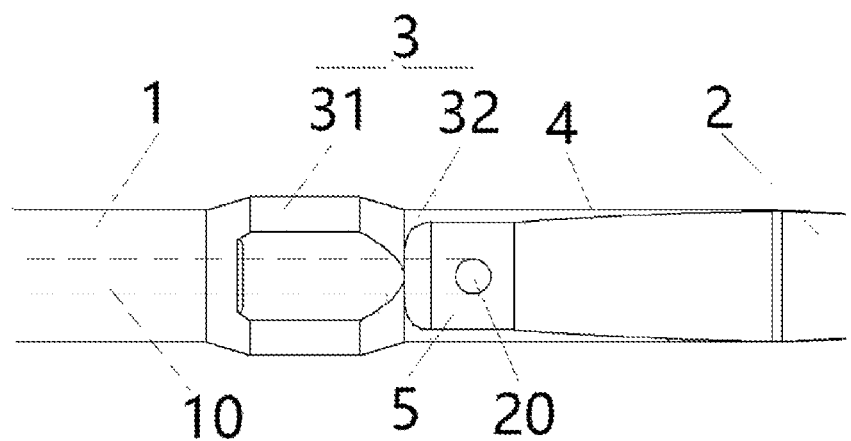
FIG. 2 is a front view showing the ultrasonic osteotome bit with the liquid injection portion according to the present invention.

FIGS. 1 and 2 show a main structure of an ultrasonic osteotome bit according to the present invention. FIG. 1 is a perspective view showing an ultrasonic osteotome bit with a liquid injection portion according to the present invention, and FIG. 2 is a front view showing the ultrasonic osteotome bit with the liquid injection portion according to the present invention. As shown in FIGS. 1 and 2, the ultrasonic osteotome bit of the present invention comprises a bit bar 1, a bit tip 2, and a liquid injection portion 3. One end of the liquid injection portion 3 is connected to the bit bar 1, and the other end of the liquid injection portion 3 is connected to the bit tip 2. The ultrasonic osteotome bit further comprises a hollow liquid injection channel 10. The hollow liquid injection channel 10 penetrates from a tail end of the bit bar 1 to the liquid injection portion 3 along an axis direction of the bit bar 1. The liquid injection portion 3 is provided with a transverse liquid guide channel 20 penetrating transversely, i.e. substantially perpendicular to the axis of the bit bar 1, and the transverse liquid guide channel 20 is in communication with the hollow liquid injection channel 10 and forms openings in lateral faces of the liquid injection portion 3.

Figure 3:
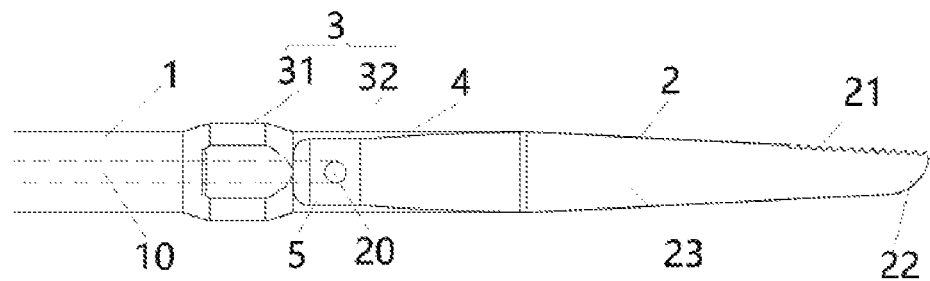
FIG. 3 is a front view of an ultrasonic osteotome bit according to a first embodiment of the present invention.
Figure 4:
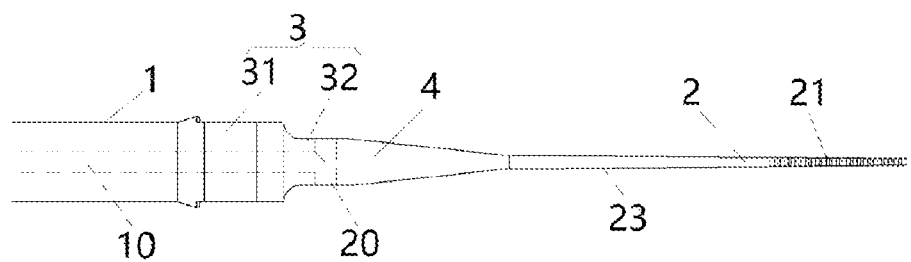
FIG. 4 is a top view of the ultrasonic osteotome bit according to the first embodiment of the present invention.
Figure 5:
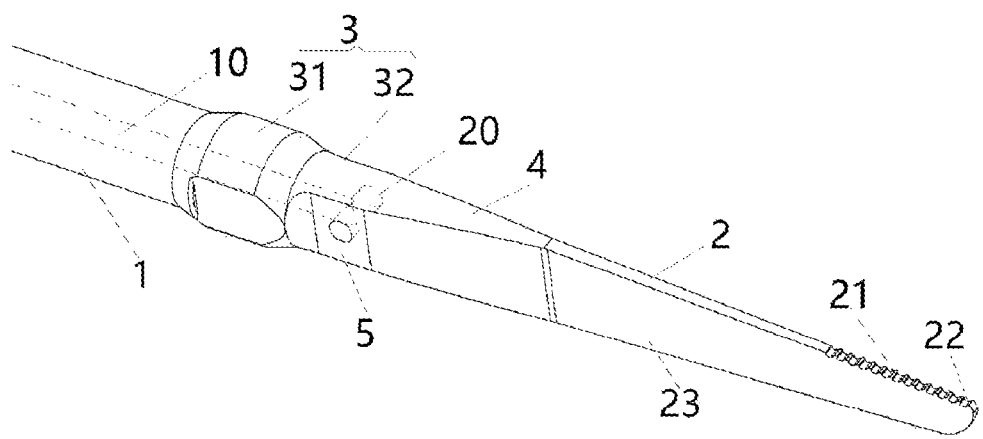
FIG. 5 is a perspective view of the ultrasonic osteotome bit according to the first embodiment of the present invention.
Figure 6:
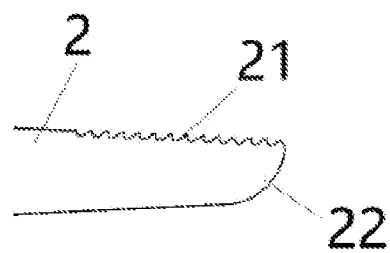
FIG. 6 is a partial enlarged view of a bit tip of the ultrasonic osteotome bit according to the first embodiment of the present invention.

FIGS. 3 to 6 show a structure of an ultrasonic osteotome bit according to a first embodiment of the present invention. FIG. 3 is a front view of an ultrasonic osteotome bit according to a first embodiment of the present invention, FIG. 4 is a top view of the ultrasonic osteotome bit according to the first embodiment of the present invention, FIG. 5 is a perspective view of the ultrasonic osteotome bit according to the first embodiment of the present invention, and FIG. 6 is a partial enlarged view of a bit tip of the ultrasonic osteotome bit according to the first embodiment of the present invention. As shown in FIGS. 3 to 6, the ultrasonic osteotome bit according to the first embodiment of the present invention comprises a bit bar 1, a bit tip 2, and a liquid injection portion 3. One end of the liquid injection portion 3 is connected to the bit bar 1, and the other end of the liquid injection portion 3 is connected to the bit tip 2. The ultrasonic osteotome bit further comprises a hollow liquid injection channel 10. The hollow liquid injection channel 10 penetrates from a tail end of the bit bar 1 to the liquid injection portion 3 along an axis direction of the bit bar 1. The liquid injection portion 3 is provided with a transverse liquid guide channel 20 penetrating transversely, i.e. substantially perpendicular to the axis of the bit bar 1, and the transverse liquid guide channel 20 is in communication with the hollow liquid injection channel 10 and forms openings in lateral faces of the liquid injection portion 3. Furthermore, in the ultrasonic osteotome bit according to the first embodiment of the present invention, a cutting portion 22 in the shape of a quarter circle is formed at a front end of the bit tip 2, and cutting teeth 21 are provided on a single side of the cutting portion 22. That is, in a normal use state, cutting teeth 21 are provided at an upper edge of the bit tip 2 of the ultrasonic osteotome bit. The cutting teeth 21 are sharp teeth, and tooth tips of the cutting teeth 21 all protrude forward in the axial direction of the bit bar 1. Of course, the present invention is not limited thereto, and the cutting teeth 21 may also be provided at a lower edge of the bit tip 2 of the ultrasonic osteotome bit.

According to the ultrasonic osteotome bit of the first embodiment of the present invention, which makes the full use of the structural characteristics of the bit, the bit bar 1 is provided with an axial hollow liquid injection channel 10, and the liquid injection portion 3 is provided with a transverse liquid guide channel 20, such that an ultrasonic cooling liquid passes through the hollow liquid injection channel 10 and flows out of the openings in the lateral faces of the transverse liquid guide channel 20, and thus sufficiently flows to the bit without being excited and scattered by ultrasonic vibration, thereby ensuring that the bit tip 2 is sufficiently cooled during use. In order to enhance the cutting performance of the ultrasonic osteotome bit, a cutting portion 22 may also be formed at the front end of the bit tip 2. Cutting teeth 21 may be further formed on a single side of a blade of the bit tip 2, and tooth tips of the cutting teeth 21 protrude forward in the axial direction of the bit bar 1. In this way, the ultrasonic cooling liquid flow can be excited forward when flowing to the tooth tips, and will not be excited and scattered to the surroundings, which further improves the cooling efficiency of the ultrasonic osteotome bit. Ultrasonic energy can also be more concentrated to a cutting site to improve the cutting efficiency.

Moreover, in the ultrasonic osteotome bit according to the first embodiment of the present invention, the liquid injection portion 3 and the bit tip 2 preferably have different thicknesses, and the liquid injection portion 3 is connected transitionally to the bit tip 2 via a wedge-shaped transition portion 4. The ultrasonic cooling liquid, which has flowed out of the openings in the lateral faces of the transverse liquid guide channel 20, flows along the wedge-shaped transition portion 4 and sufficiently flows to the bit tip 2 without being excited or scattered by ultrasonic vibration, thereby ensuring that the bit tip 2 is sufficiently cooled during use. The wedge-shaped transition portion 4 is used to connect the liquid injection portion 3 with the bit tip 2, and can also ensure the integrity of the bit structure, thereby ensuring the strength and service life of the bit, avoiding the risk of fragmentation of the bit when being broken, and improving the surgical safety. Preferably, the angle between an inclined plane of the wedge-shaped transition portion 4 and the axis direction of the bit tip 2 is less than 10 degrees. The wedge-shaped transition portion 4 helps the ultrasonic cooling liquid to flow toward the bit tip 2, so that the bit tip 2 can be sufficiently cooled.

In addition, in the ultrasonic osteotome bit according to the first embodiment of the present invention, the liquid injection portion 3 is preferably cylindrical in shape, and is provided with a large part 31 and a small part 32 sequentially formed from the bit bar 1 to the bit tip 2. Two liquid discharge faces 5 substantially parallel to wide planes 23 of the bit tip 2 are formed on the small part 32. The two liquid discharge faces 5 are substantially parallel to each other, and the transverse liquid guide channel 20 forms the openings in the two liquid discharge faces 5 respectively. The large part 31 can effectively ensure the integrity of the bit structure, thereby ensuring the strength and service life of the bit, avoiding the risk of fragmentation of the bit when being broken, and improving the surgical safety. The small part 32 allows the ultrasonic cooling liquid, which has flowed out of the openings in the lateral faces of the transverse liquid guide channel 20, to sufficiently flow to the bit tip 2 without being excited and scattered by ultrasonic vibration, thereby ensuring that the bit tip 2 can be sufficiently cooled during use.

In addition, in the ultrasonic osteotome bit according to the first embodiment of the present invention, the bit tip 2 may be in the shape of a planar sheet with two wide planes 23 being substantially parallel to each other, or a planar wedge with two wide planes 23 forming an angle. More preferably, lateral faces of the planar wedge that are perpendicular to the two wide planes 23 are isosceles trapezoidal in shape. Of course, the lateral faces of the planar wedge that are perpendicular to the two wide planes 23 may be designed in other shapes such as a right trapezoid depending on the specific use circumstances.

Figure 7:
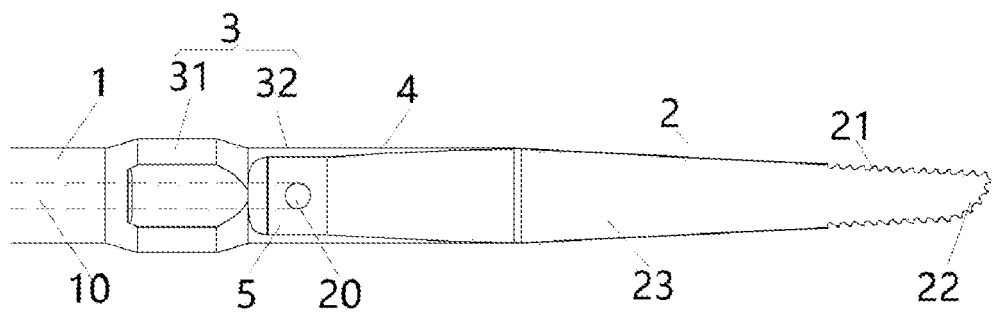
FIG. 7 is a perspective view of an ultrasonic osteotome bit according to a second embodiment of the present invention.
Figure 8:
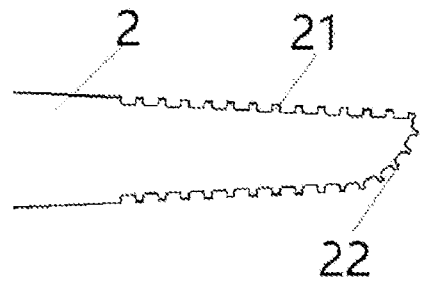
FIG. 8 is a partial enlarged view of a bit tip of the ultrasonic osteotome bit according to the second embodiment of the present invention.

FIGS. 7 and 8 show an ultrasonic osteotome bit according to a second embodiment of the present invention. FIG. 7 shows a perspective view of an ultrasonic osteotome bit according to a second embodiment of the present invention, and FIG. 8 shows a partial enlarged view of a bit tip of the ultrasonic osteotome bit according to the second embodiment of the present invention. As shown in FIG. 7, the second embodiment of the present invention is substantially the same as the first embodiment of the present invention. The ultrasonic osteotome bit according to the second embodiment of the present invention also comprises a cylindrical bit bar 1 and a sheet-shaped bit tip 2, that is, two wide planes 23 and trapezoidal planes formed due to an angle between the two wide planes 23. A liquid injection portion 3 connects the bit bar 1 with the bit tip 2. A hollow liquid injection channel 10 penetrates from a tail end of the bit bar 1 to the liquid injection portion 3 along the axis direction of the bit bar 1, and a transverse liquid guide channel 20 is provided on the liquid injection portion 3 in a direction perpendicular to the axis of the bit bar 1. The transverse liquid guide channel 20 is in communication with the hollow liquid injection channel 10, and the transverse liquid guide channel 20 forms openings in lateral faces of the liquid injection portion 3. A cutting portion 22 in the shape of a quarter circle is formed at a front end of the bit tip 2. Different from which according to the first embodiment, in the ultrasonic osteotome bit according to the second embodiment of the present invention, cutting teeth 21 are formed on both sides of a blade of the bit tip 2, that is, the cutting teeth 21 are formed on upper and lower edges of the bit tip 2 of the ultrasonic osteotome in a normal use state. The cutting teeth 21 may be sharp teeth, as shown in FIG. 7. The cutting teeth 21 may also be square teeth, as shown in FIG. 8.

According to the above structure of the ultrasonic osteotome bit of the second embodiment of the present invention, the structural characteristics of the bit can be fully used, the bit bar 1 is provided with an axial hollow liquid injection channel 10, and the liquid injection portion 3 is provided with a transverse liquid guide channel 20, such that an ultrasonic cooling liquid passes through the hollow liquid injection channel 10 and flows out of the openings in the lateral faces of the transverse liquid guide channel 20, and thus sufficiently flows to the bit without being excited or scattered by ultrasonic vibration, thereby ensuring that the bit tip 2 is sufficiently cooled during use. Moreover, the cutting teeth 21 are provided on both sides of the bit tip 2, thereby enhancing the cutting performance and service flexibility of the ultrasonic osteotome bit.

Figure 9:
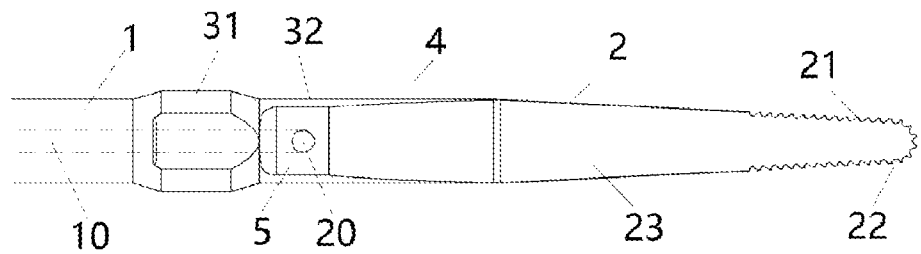
FIG. 9 is a front view of an ultrasonic osteotome bit according to a third embodiment of the present invention.

FIG. 9 shows an ultrasonic osteotome bit according to a third embodiment of the present invention. As shown in FIG. 9, the ultrasonic osteotome bit according to the third embodiment of the present invention is substantially similar to the ultrasonic osteotome bit according to the second embodiment of the present invention, except that the cutting portion 22 formed at the front end of the bit tip 2 is semicircular in shape, and cutting teeth 21 are provided on both sides of the blade of the bit tip 2. That is, in a normal use state, the cutting teeth 21 are provided on both upper and lower edges of the bit tip 2 of the ultrasonic osteotome. However, the present invention is not limited thereto. The cutting teeth 21 may also be provided on a single side of the blade of the bit tip 2, that is, the cutting teeth 21 are formed on either the upper edge or the lower edge of the bit tip 2 of the ultrasonic osteotome. Different sites can be cut by improving the shape of the bit tip 2, so that the surgical operation is more convenient.

Figure 10:
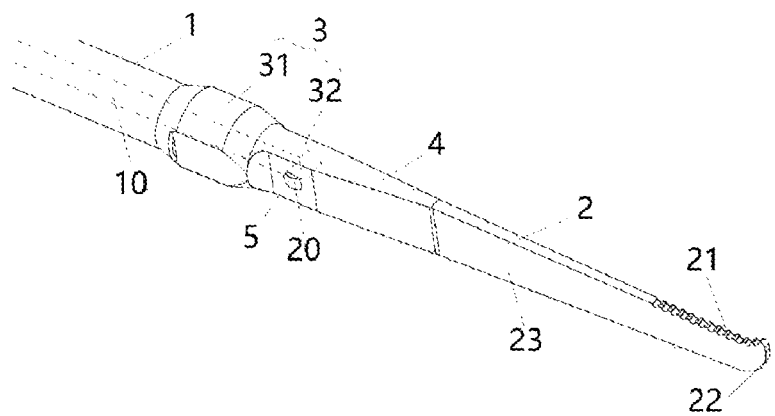
FIG. 10 is a perspective view of an ultrasonic osteotome bit according to a fourth embodiment of the present invention.
Figure 11:
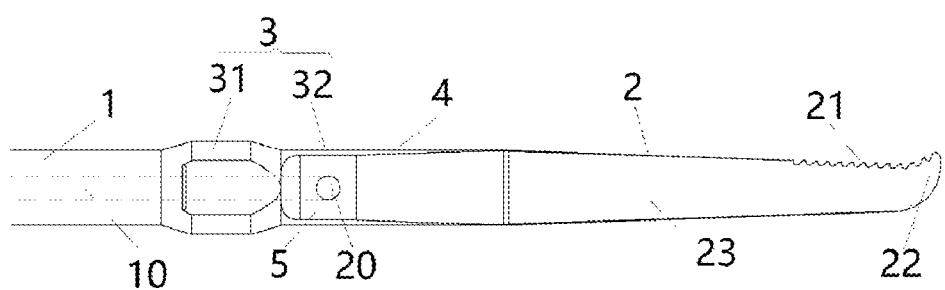
FIG. 11 is a front view of the ultrasonic osteotome bit according to the fourth embodiment of the present invention.

FIGS. 10 and 11 show an ultrasonic osteotome bit according to a fourth embodiment of the present invention. FIG. 10 is a perspective view of an ultrasonic osteotome bit according to a fourth embodiment of the present invention, and FIG. 11 is a front view of the ultrasonic osteotome bit according to the fourth embodiment of the present invention. As shown in FIGS. 10 and 11, the ultrasonic osteotome bit according to the fourth embodiment of the present invention also comprises a bit bar 1, a bit tip 2, and a liquid injection portion 3. One end of the liquid injection portion 3 is connected to the bit bar 1, and the other end of the liquid injection portion 3 is connected to the bit tip 2. The ultrasonic osteotome bit further comprises a hollow liquid injection channel 10. The hollow liquid injection channel 10 penetrates from a tail end of the bit bar 1 to the liquid injection portion 3 along the axis direction of the bit bar 1. The liquid injection portion 3 is provided with a transverse liquid guide channel 20 penetrating transversely, i.e. substantially perpendicular to the axis of the bit bar 1, the transverse liquid guide channel 20 is in communication with the hollow liquid injection channel 10, and the transverse liquid guide channel 20 forms openings in lateral faces of the liquid injection portion 3. Different from which according to the first embodiment, in the ultrasonic osteotome bit according to the fourth embodiment of the present invention, a hook-shaped cutting portion 22 is formed at the front end of the bit tip 2, and cutting teeth 21 are provided on a single side, that is, an inner side of the blade of the bit tip 2. That is, in a normal use state, the cutting teeth 21 are provided on the upper edge of the bit tip 2 of the ultrasonic osteotome. The cutting teeth 21 are sharp teeth, and tooth tips of the cutting teeth 21 all protrude forward in the axial direction of the bit bar 1. Of course, the present invention is not limited thereto, and the cutting teeth 21 may also be provided on the lower edge, that is, the outer side of the bit tip 2 of the ultrasonic osteotome bit. In addition, the cutting teeth 21 may also be square teeth.

Figure 12:
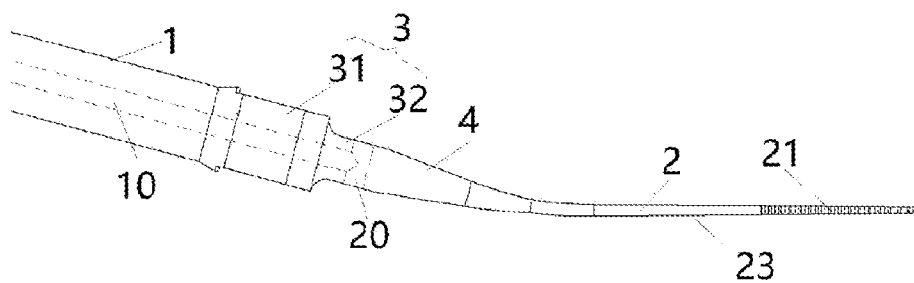
FIG. 12 is a top view of an ultrasonic osteotome bit according to a fifth embodiment of the present invention.
Figure 13:
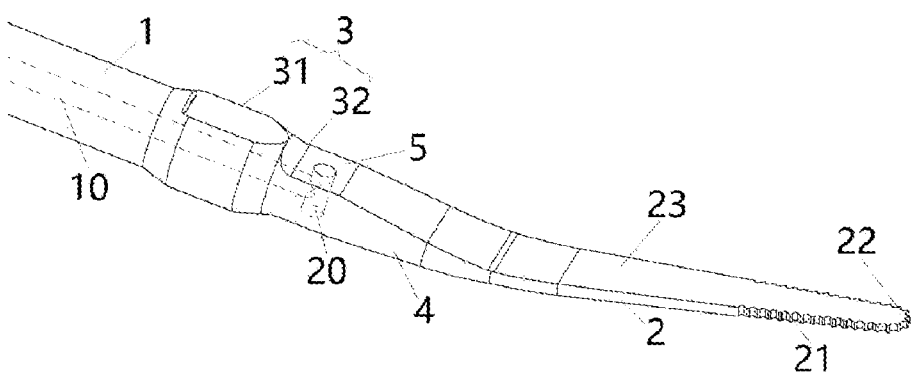
FIG. 13 is a perspective view of the ultrasonic osteotome bit according to the fifth embodiment of the present invention.

In order to enhance the versatility of the ultrasonic osteotome bit, that is, to enable operations at more surgical sites during surgery, the present invention further provides a fifth embodiment and a sixth embodiment. FIG. 12 is a top view of an ultrasonic osteotome bit according to the fifth embodiment of the present invention, and FIG. 13 is a perspective view of the ultrasonic osteotome bit according to the fifth embodiment of the present invention. As shown in FIGS. 12 and 13, the fifth embodiment of the present invention is substantially the same as the third embodiment, except that the bit tip 2 of the ultrasonic osteotome bit according to the fifth embodiment of the present invention is bent toward one side in a direction perpendicular to the wide planes 23 of the bit tip 2. Preferably, the angle between the bit tip 2 and a central axis of the bit bar 1 is 0 to 30°. In addition, as shown in FIGS. 12 and 13, the bent part of the bit tip 2 is preferably at the wedge-shaped transition portion 4, thereby ensuring the strength and service life of the ultrasonic osteotome bit and preventing the occurrence of the phenomenon that the ultrasonic osteotome bit is easily broken.

Figure 14:
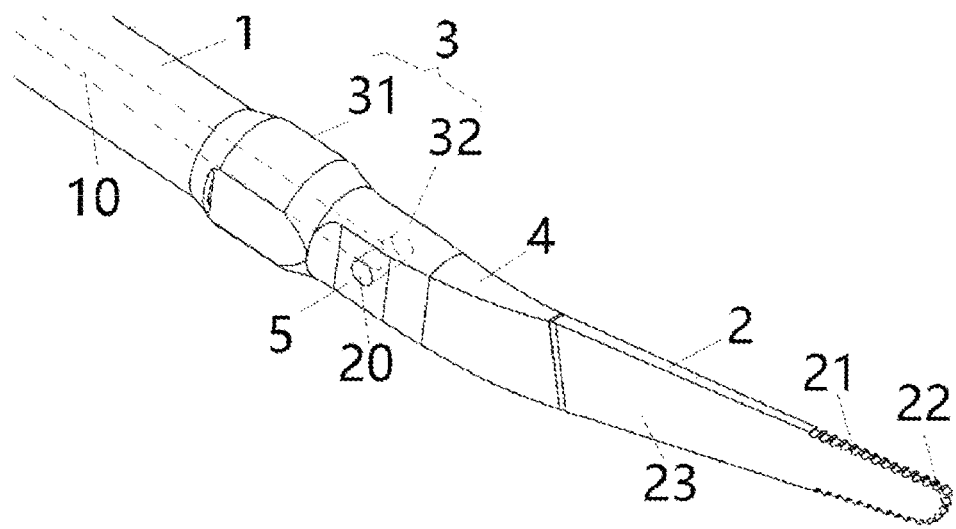
FIG. 14 is a perspective view of an ultrasonic osteotome bit according to a sixth embodiment of the present invention.
Figure 15:
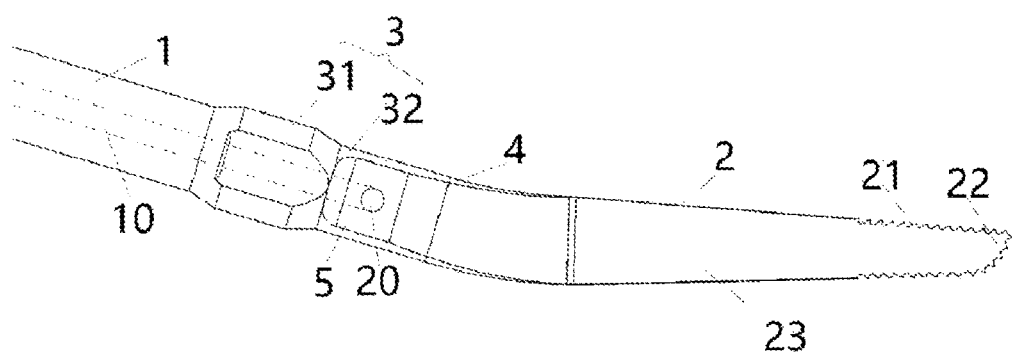
FIG. 15 is a top view of the ultrasonic osteotome bit according to the sixth embodiment of the present invention.
Figure 16:
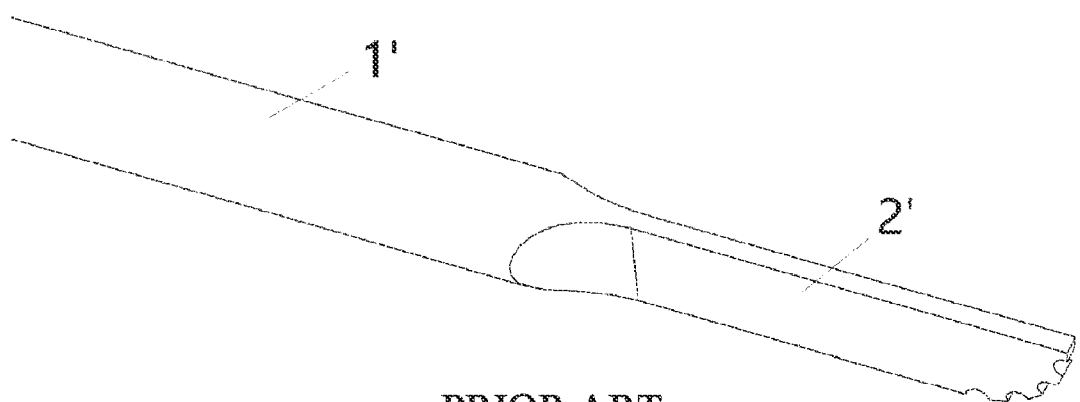
FIG. 16 is a perspective view of an ultrasonic osteotome bit cooled by a direct cooling method in the prior art.
Figure 17:
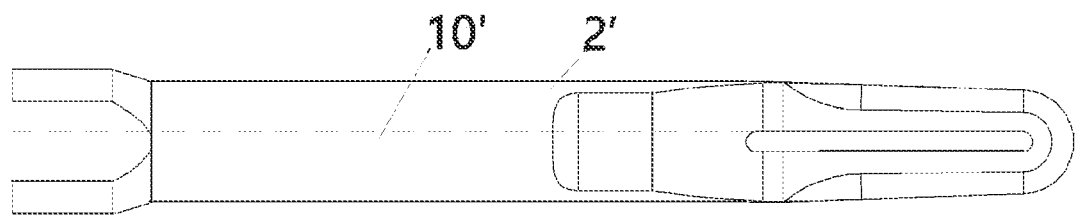
FIG. 17 is a front view of an ultrasonic osteotome bit cooled by a hollow cooling method in the prior art.

FIGS. 14 and 15 show an ultrasonic osteotome bit according to the sixth embodiment of the present invention. FIG. 14 is a perspective view of an ultrasonic osteotome bit according to the sixth embodiment of the present invention, and FIG. 15 is a top view of the ultrasonic osteotome bit according to the sixth embodiment of the present invention. As shown in FIGS. 14 and 15, the sixth embodiment of the present invention is different from the second embodiment of the present invention in that the bit tip 2 of the ultrasonic osteotome bit according to the sixth embodiment of the present invention is bent toward one side in a direction parallel to the wide planes 23 of the bit tip 2. Preferably, the angle between the bit tip 2 and a central axis of the bit bar 1 is 0 to 45°. However, the present invention is not limited thereto, and the bit tip 2 may be bent at other angles or in other directions. By designing the bit tip 2 to be bent toward one side in a direction parallel to the wide planes 23 of the bit tip 2, an operator can conveniently hold the bit, and the surgical efficiency and accuracy are prevented from being affected by operator's fatigue due to the fact that the operator's wrist is kept at the same inclination angle for a long time.

It should be noted that the foregoing six embodiments are merely representative embodiments of the ultrasonic osteotome of the present invention, and are not intended to limit the present invention. Of course, depending on the specific use circumstances, the cutting portion of the bit tip 2 may also be designed in other shapes such as a triangle, and the cutting teeth 21 may be provided on a single side of the blade of the bit tip 2 or on both sides of the blade of the bit tip 2.

In summary, the ultrasonic osteotome bit of the present invention makes the full use of the structural characteristics of the bit, the bit bar 1 is provided with an axial hollow liquid injection channel 10, and the liquid injection portion 3 is provided with a transverse liquid guide channel 20, such that an ultrasonic cooling liquid passes through the hollow liquid injection channel 10 and flows out of the openings in the lateral faces of the transverse liquid guide channel 20, and thus sufficiently flows to the bit without being excited or scattered by ultrasonic vibration, thereby ensuring that the bit tip 2 is sufficiently cooled during use. Moreover, the integrity of the bit structure can also be ensured, thereby ensuring the strength and service life of the bit, avoiding the risk of fragmentation of the bit when being broken, and improving the surgical safety. The cooling liquid reaches the bit smoothly, which can ensure that a cut bone face is kept at a rational temperature during the bone cutting process, so that the probability of necrosis of bone tissue cells can be reduced, the cut bone tissues can be healed faster, and the patient's surgical recovery time can be shortened. With this design, the shape of the bit tip is changed to meet the requirements of various surgical operation methods and sites. In addition, the cutting teeth are provided at the cutting portion of the bit tip, so that the energy of ultrasonic waves can be concentrated to the cutting site to the maximum extent, and the surgical efficiency is sufficiently ensured.

The bit tail of the ultrasonic osteotome bit of the present invention is connected to a specific ultrasonic transducer, for example, via threads, and is tightened using a corresponding wrench, and the ultrasonic transducer is then connected to a specific ultrasonic host, so that the ultrasonic osteotome bit is ready for operation.

What has been described above merely involves the specific embodiments of the present invention, but the scope of protection of the present invention is not limited thereto. Any changes or replacements that can be easily conceived by those skilled in the art within the technical scope disclosed by the present invention shall fall within the scope of protection of the present invention.

The invention claimed is:

1. An ultrasonic osteotome bit comprising:
   a bit bar (1) having a hollow liquid injection channel (10) penetrating from a tail end of the bit bar (1) along an axis of the bit bar (1),
   a bit tip (2) having wide planes (23), and
   a liquid injection portion (3), one end of the liquid injection portion (3) being connected to the bit bar (1) and the other end of the liquid injection portion (3) being connected to the bit tip (2),
   wherein the liquid injection portion (3) is provided with a transverse liquid guide channel (20) penetrating substantially perpendicular to an axis of the bit bar (1), the transverse liquid guide channel (20) is in communication with the hollow liquid injection channel (10), and the transverse liquid guide channel (20) forms openings in lateral faces of the liquid injection portion (3),
   wherein the liquid injection portion (3) is provided with a large part (31) and a small part (32) sequentially running from the bit bar (1) to the bit tip (2), and two liquid discharge faces (5) substantially parallel to the wide planes (23) of the bit tip (2) are formed on the small part (32).

2. The ultrasonic osteotome bit according to claim 1, wherein
   the liquid injection portion (3) and the bit tip (2) have different thicknesses, and the liquid injection portion (3) is connected transitionally with the bit tip (2) via a wedge-shaped transition portion (4).

3. The ultrasonic osteotome bit according to claim 2, wherein
   the angle between an inclined plane of the wedge-shaped transition portion (4) and an axis direction of the bit tip (2) is less than 10 degrees.

4. The ultrasonic osteotome bit according to claim 3, wherein
   the bit tip (2) is in the shape of a planar sheet with the two wide planes (23) being substantially parallel to each other, or in the shape of a planar wedge with the two wide planes (23) forming an angle.

5. The ultrasonic osteotome bit according to claim 4, wherein
   a cutting portion (22) is formed at a front end of the bit tip (2), and the cutting portion (22) is in the shape of a semicircle, a quarter circle, a hook, or a triangle.

6. The ultrasonic osteotome bit according to claim 4, wherein
   the bit tip (2) is bent toward one side in a direction perpendicular to the wide planes (23) of the bit tip (2).

7. The ultrasonic osteotome bit according to claim 6, wherein
   the angle between the bit tip (2) and a central axis of the bit bar (1) is 0 to 30°.

8. The ultrasonic osteotome bit according to claim 7, wherein
   the bent part of the bit tip (2) is at the wedge-shaped transition portion (4).

9. The ultrasonic osteotome bit according to claim 4, wherein
   the bit tip (2) is bent toward one side in a direction parallel to the wide planes (23) of the bit tip (2).

10. The ultrasonic osteotome bit according to claim 9, wherein
    the angle between the bit tip (2) and a central axis of the bit bar (1) is 0 to 45°.

11. The ultrasonic osteotome bit according to claim 4, wherein
    lateral faces of the planar wedge that are perpendicular to the two wide planes (23) are isosceles trapezoidal or right-angled trapezoidal in shape.

12. The ultrasonic osteotome bit according to claim 1, wherein
    cutting teeth (21) are formed on one side or two sides of a blade of the bit tip (2).

13. The ultrasonic osteotome bit according to claim 12, wherein
    the cutting teeth (21) are sharp teeth or square teeth, and tooth tips of the cutting teeth (21) all protrude forward in an axial direction of the bit bar (1).

14. The ultrasonic osteotome bit according to claim 12, wherein
    a bent part of the bit tip (2) is at a wedge-shaped transition portion (4).

15. The ultrasonic osteotome bit according to claim 1, wherein
    the liquid injection portion (3) is cylindrical in shape.

16. The ultrasonic osteotome bit according to claim 1, wherein
    the two liquid discharge faces (5) are substantially parallel to each other.

17. The ultrasonic osteotome bit according to claim 1, wherein
    the openings formed by the transverse liquid guide channel (20) are formed in the two liquid discharge faces (5) respectively.

* * * * *